(12) United States Patent
Straessler et al.

(10) Patent No.: US 8,471,041 B2
(45) Date of Patent: Jun. 25, 2013

(54) METHODS OF SYNTHESIZING AND ISOLATING N-(BROMOACETYL)-3,3-DINITROAZETIDINE AND A COMPOSITION INCLUDING THE SAME

(75) Inventors: Nicholas A. Straessler, North Salt Lake, UT (US); Louis F. Cannizzo, Ogden, UT (US); Ping Li, Brigham City, UT (US); Michael P. Kramer, Wellsville, UT (US); David M. Rosenberg, North Ogden, UT (US)

(73) Assignee: Alliant Techsystems Inc., Arlington, VA (US)

( * ) Notice: Subject to any disclaimer, the term of this patent is extended or adjusted under 35 U.S.C. 154(b) by 512 days.

(21) Appl. No.: 12/702,782

(22) Filed: Feb. 9, 2010

(65) Prior Publication Data

US 2011/0195947 A1   Aug. 11, 2011

(51) Int. Cl.
  *C07D 205/04* (2006.01)
(52) U.S. Cl.
  USPC .......................................................... 548/953
(58) Field of Classification Search
  USPC .......................................................... 548/953
  See application file for complete search history.

(56) References Cited

U.S. PATENT DOCUMENTS

| | | | |
|---|---|---|---|
| 3,845,770 A | 11/1974 | Theeuwes et al. | |
| 3,916,899 A | 11/1975 | Theeuwes et al. | |
| 4,765,539 A | 8/1988 | Noakes et al. | |
| 5,112,598 A | 5/1992 | Biesalski | |
| 5,336,784 A | 8/1994 | Hiskey et al. | |
| 5,521,203 A | 5/1996 | Adams et al. | |
| 5,556,611 A | 9/1996 | Biesalki | |
| 5,579,458 A | 11/1996 | Yokosuks et al. | |
| 5,580,988 A | 12/1996 | Dave | |
| 5,693,794 A | 12/1997 | Nielsen | |
| 5,698,155 A | 12/1997 | Grosswald et al. | |
| 5,950,619 A | 9/1999 | Van der Linden et al. | |
| 5,954,047 A | 9/1999 | Armer et al. | |
| 5,970,974 A | 10/1999 | Van Der Linden et al. | |
| 6,056,966 A | 5/2000 | Selim et al. | |
| 6,133,320 A | 10/2000 | Yallampalli et al. | |
| 6,245,799 B1 | 6/2001 | Asselin et al. | |
| 6,407,236 B1 | 6/2002 | Baraldi et al. | |
| 7,163,958 B2 | 1/2007 | Earl et al. | |
| 7,507,842 B2 | 3/2009 | Bednarski et al. | |
| 7,745,643 B2 | 6/2010 | Cannizzo et al. | |
| 2002/0137770 A1 | 9/2002 | Nara et al. | |
| 2004/0024057 A1 | 2/2004 | Earl et al. | |
| 2004/0138481 A1 | 7/2004 | Highsmith et al. | |
| 2004/0167212 A1 | 8/2004 | Bednarski et al. | |
| 2006/0111272 A1 | 5/2006 | Roberts et al. | |
| 2007/0135384 A1* | 6/2007 | Bednarski et al. | .............. 514/79 |
| 2008/0255149 A1 | 10/2008 | Dobler et al. | |
| 2009/0093644 A1 | 4/2009 | Cannizzo et al. | |
| 2012/0149678 A1 | 6/2012 | Oronsky et al. | |

FOREIGN PATENT DOCUMENTS

| | | |
|---|---|---|
| DE | 10111049 A1 | 9/2002 |
| EP | 0412211 A1 | 2/1991 |
| EP | 1336602 | 8/2003 |
| JP | 60116642 | 6/1985 |
| WO | 9532715 A1 | 12/1995 |
| WO | 9636602 | 11/1996 |
| WO | 98/16485 A1 | 4/1998 |
| WO | 9916436 A1 | 4/1999 |
| WO | 9959575 A1 | 11/1999 |
| WO | 00/06143 A1 | 2/2000 |
| WO | 0177100 | 10/2001 |
| WO | 2004032864 | 4/2004 |
| WO | 2004098538 | 11/2004 |
| WO | 2004113281 | 12/2004 |
| WO | 2005046661 A2 | 5/2005 |
| WO | 2007/022121 A2 | 2/2007 |
| WO | 2007/022225 A2 | 2/2007 |
| WO | 2007022121 | 2/2007 |
| WO | 2007022225 | 2/2007 |

OTHER PUBLICATIONS

Ansari, Nabi G., et al., Primary squamous cell carcinoma of the prostate: a rare clinicopatholigical entity. Report of 2 cases and review of literature, Urol. Int., 2001, pp. 216-219, vol. 66, No. 4 (abstract).

Granelli, Paola, SEL1L and Squamous Cell Carcinoma of the Esophagus, Clinical Cancer Research, Sep. 1, 2004, pp. 5857-5861, vol. 10.

Lopez-Ferrer, Anna, et al., Differences in the O-Glycosylation Patterns Between Lung Squamous Cell Carcinoma and Adenocarcinoma, Am. J. Clin. Pathol., 2002, pp. 749-755, vol. 118, American Society for Clinical Pathology.

(Continued)

*Primary Examiner* — Samantha Shterengarts
(74) *Attorney, Agent, or Firm* — TraskBritt (57) ABSTRACT

A method of synthesizing and isolating N-(bromoacetyl)-3,3-dinitroazetidine (ABDNAZ) by reacting DNAZ with bromoacetyl bromide and boron trifluoride etherate to produce a mixture comprising ABDNAZ and a salt of DNAZ. Water and a solvent are added to the mixture to form an organic phase comprising the ABDNAZ and an aqueous phase comprising the salt of DNAZ. The organic phase and the aqueous phase are separated to produce an ABDNAZ/solvent solution comprising the ABDNAZ and the aqueous phase comprising the salt of DNAZ. A nonsolvent is added to the ABDNAZ/solvent solution to produce an ABDNAZ/solvent/nonsolvent mixture. The ABDNAZ is subsequently recovered. A composition comprising ABDNAZ is also disclosed.

17 Claims, 2 Drawing Sheets

OTHER PUBLICATIONS

Hockel, Michael, et al., Tumor Hypoxia: Definitions and Current Clinical, Biologic, and Molecular Aspects, Journal of the National Cancer Institute, Feb. 21, 2001, pp. 266-276, vol. 93, No. 4.

Maxwell, P.H., et al., Hypoxia-inducible factor-1 modulates gene expression in solid tumors and influences both angiogenesis and tumor growth, Proc. Natl. Acad. Sci. USA, Jul. 1997, pp. 8104-8109, vol. 94, Medical Sciences.

Shokeir, A.A., Squamous Cell Carcinoma of the Bladder: pathology, diagnosis and treatment, BJU International, Jan. 2004, pp. 216-220, vol. 93.

Yen, Tzu-Chen, et al., F-FDG Uptake in Squamous Cell Carcinoma of the Cervix Is Correlated with Glucose Transporter 1 Expression, The Journal of Nuclear Medicine, Jan. 2004, pp. 22-29, vol. 45, No. 1.

Alderman, D.A., "A Review of Cellulose Ethers in Hydrophilic Matrices for Oral Controlled-Release Dosage Forms," Int. J. Pharm. Tech. & Prod. Mfr., vol. 5, No. 3, pp. 1-9, 1984.

Archibald, T.G., et al., "Synthesis and X-ray Crystal Structure of 1,3,3-Trinitroazetidine," J. Org. Chem, vol. 55, 1990, pp. 2920-2924.

Bamba, Morifere, et al., "Release Mechanisms in Gelforming Sustained Release Preparations," Int. J. Pharm., vol. 2, 1979, pp. 307-315.

Chawla, Garima, et al., "Challenges in Polymorphism of Pharmaceuticals," CRIPS, vol. 5, No. 1, Jan.-Mar. 2004, pp. 9-12.

Dave, Paritosh R., "Acylative Dealkylation of N-tert-Butyl-3-substituted Azetidines: Facile Access to [1.1.0] Azabicyclobutane, 3-Hydroxyazetidinium Hydrochloride, and 3-Azetidinones," J. Org. Chem., vol. 61, 1996, pp. 5453-5455.

During, Matthew J., et al., "Controlled Release of Dopamine from a Polymeric Brain Implant: In Vivo Characterization," Annals of Neurology, vol. 25, No. 4, Apr. 1989, pp. 351-356.

Goodson, J. Max, "Dental Applications," Chapter 6 of Medical Applications of Controlled Release, vol. II, pp. 115-138, CRC Press, Inc., Boca Raton, FL, copyright 1984.

Howard, Matthew A., III, et al., "Intracerebral Drug Delivery in Rats with Lesion-Induced Memory Deficits," J. Neurosurg., vol. 71, pp. 105-112, 1989.

Huguenin, Sandra, et al., "Evaluation of the antitumoral potential of different nitric oxide-donating non-steroidal anti-inflammatory drugs (NO-NSAIDs) on human urological tumor cell lines," Cancer Letters, vol. 218, 2005, pp. 163-170.

Jia, Q., et al., "NO donors with anticancer activity," Expert Opinion on Therapeutic Patents, vol. 12, No. 6 (2002), pp. 819-826, Great Britain.

Konovalova, N.P., et al., "Nitric oxide donor increases the efficiency of cytostatic therapy and retards the development of drug resistance," Nitric Oxide, vol. 8, No. 1 (Feb. 2003), pp. 59-64.

Langer, Robert S., et al., eds., "Medical Applications of Controlled Release," vol. 1, Classes of Systems, Ch. 2, pp. 42-67, CRC Press, Inc., Boca Raton, FL, copyright 1984.

Langer, Robert, "New Methods of Drug Delivery," Science, New Series, vol. 249, No. 4976, Sep. 28, 1990, pp. 1527-1533.

Langer, Robert, et al., "Chemical and Physical Structure of Polymers as Carriers for Controlled Release of Bioactive Agents: A Review," JMS—Rev. Macromol. Chem. Phys., Ch. 23, pp. 61-126, 1983.

Levy, Robert J., "Inhibition of Calcification of Bioprosthetic Heart Valves by Local Controlled-Release Diphosphonate," Science, New Series, vol. 228, No. 4696, Apr. 12, 1985, pp. 190-192.

Ling, C., et al., "Phase I study of CM-Na combined with concurrent radiochemotherapy for advanced esophageal carcinoma (abstract)," Chinese Journal of Cancer, vol. 24, No. 5 (May 2005), (U.S. National Library of Medicine, Bethesda, MD, May 2005).

Muehlstaedt et al., caplus an 1976:89768.

Naimi, Ebrahim, et al., "Synthesis of 3'- and 5'-Nitrooxy Pyrimidine Nucleoside Nitrate Esters: "Nitric Oxide Donor" Agents for Evaluation as Anticancer and Antiviral Agents," J. Med. Chem., vol. 46, 2003, pp. 995-1004.

Newman, Ann W., et al., "Solid-state analysis of the active pharmaceutical ingredient in drug products," DDT, vol. 8, No. 19, Oct. 2003, pp. 898-905.

Raleigh, R.D., Verschoyle, C., et al., "Pharmacokinetics of Isotretinoin (ISO) in Rats Following Oral Dosing or Aerosol Inhalation," British J. Cancer, vol. 80, Suppl. 2, 96, 1999, p. 269.

Remington, "The Science and Practice of Pharmacy," 19th Edition, vol. II, pp. 1495-1562, 1577-1614, and 1660-1692, Mack Publishing Company, Easton, PA, 1995.

Rosenthal, David I., "A Phase I Single-Dose Trial of Gadolinium Texaphyrin (Gd-Tex), a Tumor Selective Radiation Sensitizer Detectable by Magnetic Resonance Imaging," Clinical Cancer Research, vol. 5, No. 4, pp. 739-745, Apr. 1999.

Sandler, G., "Clinical evaluation of propatylnitrate in angina pectoris," British Medical Journal, vol. 2, No. 5269 (Dec. 30, 1961), pp. 1741-1744.

Sauder, Christopher D., "A Preliminary Trial of the Programmable Implantable Medication System for Insulin Delivery," The New England Journal of Medicine, vol. 321, No. 9, pp. 574-579, Aug. 31, 1989.

Sefton, Michael V., "Implantable Pumps," CRC Crit. Rev. Biomed. Eng., vol. 14, No. 3, pp. 201-237, 1987.

Smolen, Victor F., et al., eds., "Controlled Drug Bioavailability," vol. 1, Drug Product Design and Performance, Ch. 7, pp. 203-237, John Wiley & Sons, New York, NY, copyright 1984.

Stamler, J.S., et al., "Inhaled ethyl nitrite gas for persistent pulmonary hypertension in infants," The Lancet, Lancet Limited, vol. 360, No. 9350 (Dec. 21, 2002), p. 2077, Great Britain.

Treat, Joseph, et al., "Liposome Encapsulated Doxorubicin Preliminary Results of Phase I and Phase II Trials," Liposomes in the Therapy of Infectious Diseases and Cancer, Proceedings of the Ciba-Geigy-Squibb-UCLA Colloquium at Lake Tahoe, CA, Feb. 16-20, 1988, pp. 353-365.

Verma, R.K., et al., "Osmotically Controlled Oral Drug Delivery," Drug Dev. Ind. Pharm., vol. 26, No. 7, 2000, pp. 695-708.

Electrochemical Oxidation of Alkylnitro Compounds PP-1345, A SERDP 'SEED' Activity, initial submission Jun. 30, 2004; amended Aug. 17, 2004; points of contact Scott K. Lusk and Alan N. Green.

International Search Report for PCT/US2011/021500, mailed May 3, 2011.

Written Opinion of the International Searching Authority for PCT/US2011/021500, mailed May 3, 2011.

Written Opinion of the International Searching Authority for PCT/US06/31722 mailed May 29, 2007.

Written Opinion of the International Searching Authority for PCT/US06/31917 mailed Jul. 20, 2007.

Hiskey, Michael A., et al., Preparation of 1-Substituted-3,3-Dinitroazetidines, Journal of Energetic Materials, 1999, pp. 233-254, vol. 17, Dowden, Brodman & Devine, Inc.

Crowder et al., Caplus an 1999: 171384.

Dave, P.R. et al., "Convenient Acylative Dealkylation of Tertiary Amines," Journal of Organic Chemistry, 2000, vol. 65, pp. 1207-1209.

Examination Report for Australian patent Application No. 2006279589, dated May 18, 2012.

Hiskey et al., caplus an 1993:233785.

Hiskey et al., caplus an 1994:700750.

McKenney et al., "Synthesis and Thermal properties of 1,3,3-Trinitroazetidine (TNAZ), Related 3,3-Dinitroazetidium Salts, and 15N, 13C, and 2H Isotopomers," Journal of Physical Chemistry A, 1997, vol. 101, No. 24, pp. 4375-4383.

Sikder et al., "1,3,3-Trinitroazetidine (TNAZ), a melt-cast explosive: synthesis, characterization and thermal behavior," Journal of Hazardous Materials, vol. 113, 2004, pp. 35-43.

Nicolescu Adreian et al. ,"Organic nitrites and NO: inhibition of lipid peroxidation and radical reactions," Chemical Research in Toxicology, Feb. 2004, pp. 185-196, vol. 17, No. 2.

Kaplan D. L. et al. "Biodegradation of glycidol and glycidyl nitrate," Applied and Environmental Microbilogy, 1982, pp. 144-150, vol. 43, No. 1.

Zimmerman et al., "Pharmacological comparison of the steroisomers of glyceryl-1-nitrate," Arzneimittel-Forschung, 1994, pp. 474-477, Vo.. 44, No. 4.

Eremenko, L.T. et al., "Synthesis of tetranitrates of conduritol-E and .alpha.-epoxy conduritol-E," Chemical Abstracts Service, retrieved from STN database accession No. 73:66844 (1970).

Zhang et al, Caplus an 1998:460439.

PCT International Search Report for International Application PCT/US2006/031917, Publication WO/2007/022225, dated Jul. 20, 2007.

PCT International Search Report for International Application PCT/US2006/031722, Publication WO/2007/022121, dated May 29, 2007.

Armstrong, JS, et al., Role of Glutathione Depletion and Reactive Oxygen Species Generation in Apoptotic Signaling in a Human B Lymphoma Cell Line, Cell Death and Differentiation, 2002, pp. 252-263, vol. 9, Nature Publishing Group.

Berge, Stephen M., et al., Pharmaceutical Salts, Journal of Pharmaceutical Sciences, Jan. 1977, pp. 1-19, vol. 66, No. 1.

Brown, J. Martin, et al., Tirapazamine: Laboratory Data Relevant to Clinical Activity, Anti-Cancer Drug Design, 1998, pp. 529-539, vol. 13.

Nitrates and Nitrites Answers to Frequently Asked Questions, Ohio Bureau of Environmental Health, Health Assessment Section, Nov. 1, 2006, 2 pages.

Ignarro, Louis J., Nitric Oxide Biology and Pathology, 2000, pp. 5, 895, and 908 Academic Press.

Johnson, J.. et al., Relationships Between Drug Activity in NCI Preclinical in Vitro and in Vivo Models and Early Clinical Trials, British Journal of Cancer, 2001, pp. 1424-1431, vol. 84, No. 10.

Kashfi, Khosrow, et al., Nitric Oxide-Donating Nonsteroidal Anti-Inflammatory Drugs Inhibit the Growth of Various Cultured Human Cancel Cells: Evidence of a Tissue Type-Independent Effect, The Journal of Pharmacology and Experimental Therapeutics, 2002, pp. 1273-1282, vol. 303, No. 3.

Mendenhall, William M., et al., Radiation Therapy for Squamous Cell Carcinoma of the Tonsillar Region: A Preferred Alternative to Surgery?, Journal of Clinical Oncology, Jun. 2000, pp. 2219-2225, vol. 18, No. 11.

Ning, Shoucheng, et al., The Antiangiogenic Agents SU5416 and SU6668 Increase the Antitumor Effects of Fractionated Irradiation, Radiation Research, 2002, pp. 45-51, vol. 157.

Rupnow, Brent A, et al., p53 Mediates Apoptosis Induced by C-Myc Activation in Hypoxic or Gamma Irradiated Fibroblasts, Cell Death and Differentiation, 1998, pp. 141-147, vol. 7.

Sausville, Edward A., et al., Contributions of Human Tumor Xenografts to Anticancer Development, Cancer Research, 2006, pp. 3351-3354, vol. 66, No. 7.

Stratford, Ian J., et al., Bioreductive Drugs into the Next Millennium, Anti-Cancer Drug Design, 1998 pp. 519-528, vol. 13.

Morales-Suarez-Varela, Maria M., et al., Impact of Nitrates in Drinking Water on Cancel Mortality in Valencia, Spain, European Journal of Epidemiology, 1995, pp. 15-21, vol. 11.

Prezioso, J.A., et al., Genetic Toxicity Evaluation of 1, 3, 3-Trinitroazetidine, vol. IV: Summary Report on the Genotoxicity of TNAZ, AL/OE-TR-1994-0069 vol. IV of IV, Oct. 1994, 22 pages, Air Force Materiel Command, Wright-Patterson Air Force Base, Ohio.

Simpson, R.L., et al., Characterization of TNAZ, UCRL-ID-119672, Dec. 14, 1994, Lawrence Livermore National Laboratory, 15 pages.

Watt, Duncan S., et al., Evaluation of 1,3,3-Trinitrozaetidine (TNAZ)—A High Performance Melt-Catable Explosive, Weapons Systems Division Aeronautical and Maritime Research Laboratory, Report No. DSTO-TR-1000, issue date Jul. 2000, 34 pages.

Watt, Duncan S., et al., TNAZ Based Melt-Cast Explosives: Technology Review and AMRL Research Directions, Weapons Systems Division Aeronautical and Maritime Research Laboratory, Report DSTO-TR-0702, issue date Jul. 1987, 37 pages.

Wilson, William R., et al., Radiation-Activated Prodrugs as Hypoxia-Selective Cytotoxins: Model Studies with Nitroarylmethyl Quaternary Salts, Anti-Cancer Drug Design, 1998, pp. 663-685, vol. 13.

West, Anthony R., Solid State Chemistry and its Applications, 1988, pp. 358, and 365, Wiley, New York.

Yamaguchi, A., et al., Photodynamic Therapy with Motexafin Lutetium (Lu-Tex) Reduces Experimental Graft Coronary Artery Disease, Transplantation, Jun. 15, 2001, pp. 1526-1532, vol. 71, No. 11 (abstract).

Akhavan, Jacqueline, Explosives and Propellants, Kirk-Othmer Encyclopedia of Chemical Technology, Sep. 17, 2004, pp. 719-744.

Kornblum et al., "Oxidative Substitution of Nitroparaffin Salts," J. Org. Chem., 1983, vol. 48, pp. 332-337.

Cai, T.B. et al., Expert Opinion on Therapeutic Patents, 2004, vol. 14, No. 6, p. 849-857 (Abstract Only).

Cook T. et al., Cancer Research, 2004, vol. 64, No. 21, p. 8015-21.

Garver, L, et al., "Catalyzed Oxidative Nitration of Nitronate Salts," J. Org. Chem., 1985, vol. 50, pp. 1699-1702, © American Chemical Society.

Katritzky, A. et al., "Novel Syntheses of 1,3,3-Trinitroazetidine," J. Heterocyclic Chem., 1994, vol. 31, 271, 1994, pp. 271-275.

Marchand, A. et al., "A Novel Approach to the Synthesis of 1,3,3-Trinitroazetidine," J. Org. Chem., 1995, vol. 60 pp. 4943-4946, © American Chemical Society.

Needleman, P. et al., Relationship Between Glutathione-Dependent Denitration and the Vasodilator Effectiveness of Organic Nitrates, J. of Pharmacology and Exptl. Therapeutics, 165, 2, 1969, pp. 286-288.

Straessler, N., et al., "Development of a Safe and Efficient Two-Step Synthesis for Preparing 1-Bromoacetyl-3,3-dinitroazetidine, a Novel Clinical Anticancer Candidate," Org. Process Res. Dev., 2012, vol. 16, pp. 512-517, © American Chemical Society.

International Search Report for PCT/US2011/064178 mailed Apr. 17, 2012, 4 pages.

International Written Opinion for PCT/US2011/064178 mailed Apr. 17, 2012, 4 pages.

International Search Report for PCT/US2012/038592 mailed Aug. 10, 2012, 5 pages.

International Written Opinion for PCT/US2012/038592 mailed Aug. 10, 2012, 5 pages.

Crowder et al., Vibrational analysis of high-energy compounds: 1,3,3-trinitroazetidine and 1-acetyl-3, 3-dinitroazetidine, Journal of Energetic Materials (1999) vol. 17, 49-68.

* cited by examiner

METHODS OF SYNTHESIZING AND ISOLATING N-(BROMOACETYL)-3,3-DINITROAZETIDINE AND A COMPOSITION INCLUDING THE SAME

CROSS-REFERENCE TO RELATED APPLICATIONS

This application is related to U.S. patent application Ser. No. 12/252,278, filed Oct. 15, 2008, now U.S. Pat. No. 7,745, 643, issued Jun. 29, 2012, which is a divisional of U.S. patent application Ser. No. 11/502,810, filed Aug. 11, 2006, now U.S. Pat. No. 7,507,842, issued Mar. 24, 2009, which application claims priority to U.S. Provisional Application No. 60/707,851, filed Aug. 12, 2005, the disclosure of each of which is incorporated herein in its entirety by reference.

TECHNICAL FIELD

Embodiments of the present invention relate to a method of synthesizing and isolating N-(bromoacetyl)-3,3-dinitroazetidine (ABDNAZ). More specifically, embodiments of the present invention relate to a method of synthesizing and isolating ABDNAZ that produces a higher purity and higher yield of ABDNAZ relative to conventional methods. Embodiments of the present invention also relate to a composition including the ABDNAZ.

BACKGROUND

Cyclic nitro compounds, such as ABDNAZ, are being investigated for their potential use in treating cancer. Methods of synthesizing ABDNAZ have been described, such as in U.S. Pat. No. 7,507,842 to Bednarski et al. ("Bednarski"). In Bednarski, ABDNAZ is synthesized by reacting 1-tert-butyl-3,3-dinitroazetidine (DNAZ) with bromoacetyl bromide in the presence of boron trifluoride etherate. For every mole of ABDNAZ produced, a mole of a hydrogen bromide salt of DNAZ (DNAZ HBr) is also produced as a coproduct. The ABDNAZ is isolated from the DNAZ HBr by cooling the reaction mixture, adding dichloromethane, and filtering the DNAZ HBr. Solid DNAZ HBr is sensitive to impact, friction, and other external stimuli and, therefore, must be handled carefully. The dichloromethane filtrate is washed with water, dried, and then the dichloromethane is evaporated, producing a crude ABDNAZ mixture. The product is washed sequentially with diethyl ether and dried under vacuum, yielding ABDNAZ that is approximately 98% pure and at a yield of approximately 75% (based on bromoacetyl bromide). The 2% of impurities remaining in the ABDNAZ are believed to include bromoacetic acid, unreacted DNAZ, and DNAZ HBr. This method of producing ABDNAZ is referred to herein as the Bednarski process. While the Bednarski process provides ABDNAZ at a reasonable purity and yield, the purity does not meet current industry standards for pharmaceutical uses. In addition, solid DNAZ HBr produced during the Bednarski process is an explosive compound, which adds to the complexity of producing ABDNAZ.

It would be desirable to synthesize and isolate ABDNAZ by a process that minimizes or reduces hazards associated with handling explosive intermediates, such as DNAZ HBr. The resulting ABDNAZ would have a comparable or higher yield and purity relative to that produced by the Bednarski process.

BRIEF SUMMARY

An embodiment of the invention comprises a method of producing ABDNAZ. The method includes reacting DNAZ with bromoacetyl bromide and boron trifluoride etherate to produce a reaction mixture comprising ABDNAZ and a salt of DNAZ. Water and a solvent are added to the reaction mixture to form an organic phase comprising the ABDNAZ and an aqueous phase comprising the salt of DNAZ. The organic phase and the aqueous phase are separated to produce an ABDNAZ/solvent solution comprising the ABDNAZ and the aqueous phase comprising the salt of DNAZ. A nonsolvent is added to the ABDNAZ/solvent solution to produce an ABDNAZ/solvent/nonsolvent mixture. The ABDNAZ is subsequently recovered.

Another embodiment of the invention comprises another method of producing ABDNAZ. The method includes reacting DNAZ with bromoacetyl bromide and boron trifluoride etherate in dichloromethane to produce a reaction mixture comprising ABDNAZ and a hydrogen bromide salt of DNAZ. Water and an additional volume of dichloromethane are added to the reaction mixture to form an organic phase comprising the dichloromethane and the ABDNAZ and an aqueous phase comprising the water and the hydrogen bromide salt of DNAZ. The organic phase is separated from the aqueous phase and ethanol is added to the organic phase comprising the dichloromethane and the ABDNAZ. The dichloromethane is evaporated under reduced pressure to form an ABDNAZ/ethanol suspension. The ethanol is then filtered from the ABDNAZ/ethanol suspension.

A further embodiment of the invention comprises a composition comprising ABDNAZ at a purity of greater than approximately 99.5% and a pharmaceutically effective vehicle.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction with the accompanying drawings in which:

DETAILED DESCRIPTION

A method of synthesizing and isolating ABDNAZ is disclosed. The ABDNAZ is produced at a higher yield than in the Bednarski process. The ABDNAZ produced also has a higher purity than that produced in the Bednarski process. In addition, the method of the present invention eliminates the handling of solid explosive intermediates that are impact and friction sensitive. The method of the present invention also reduces the total number of acts in the process.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the invention and such term is used in preference to the more restrictive term "is" so as to avoid any implication that other, compatible materials, structures, features and methods usable in combination therewith should, or must be, excluded.

Figure 1:
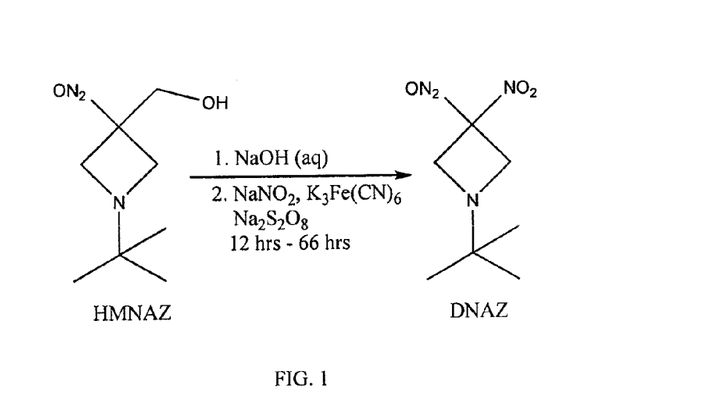
FIG. 1 illustrates the reaction of 1-tert-butyl-3-hydroxymethyl-3-nitroazetidine (HMNAZ) to produce DNAZ.
Figure 2:
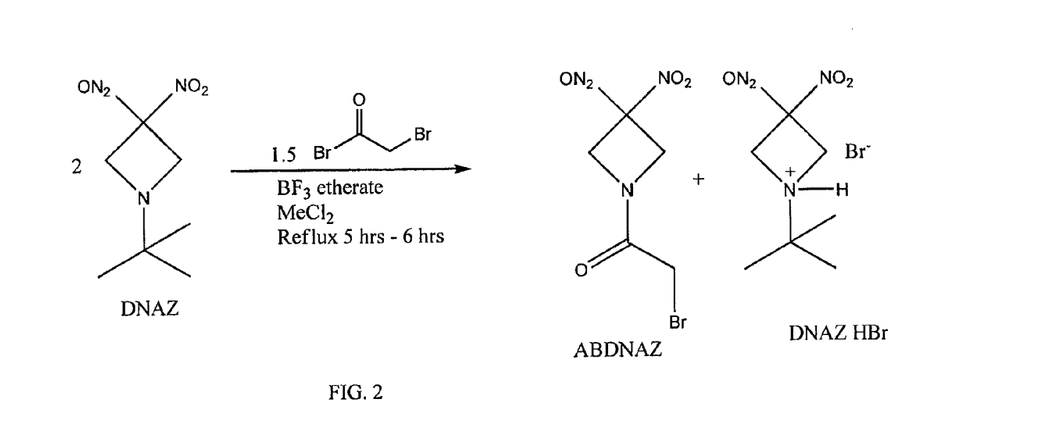
FIG. 2 illustrates the reaction of DNAZ to produce ABDNAZ.

ABDNAZ may be synthesized by an oxidative nitration of 1-tert-butyl-3-hydroxymethyl-3-nitroazetidine (HMNAZ), producing 1-tert-butyl-3,3-dinitroazetidine (DNAZ), as shown in FIG. 1. The oxidative nitration reaction may be conducted for from approximately three hours to approximately seventy-four hours at a temperature of less than or equal to approximately 30° C. The DNAZ may then be reacted with bromoacetyl bromide in the presence of boron trifluoride etherate in a solvent, producing ABDNAZ and DNAZ HBr, as shown in FIG. 2. For every one half molar equivalent of DNAZ that is converted to ABDNAZ, another one half molar equivalent of the DNAZ functions as an acid scavenger and forms DNAZ HBr. As used herein, the term "solvent" means and includes an organic solvent in which the DNAZ and ABDNAZ are substantially soluble and which is substantially miscible with a nonsolvent used to crystallize the ABDNAZ. The solvent and nonsolvent may have sufficiently different boiling points such that the solvent is easily removed at a subsequent point in the synthesis. While embodiments herein describe the solvent as dichloromethane, other organic solvents having the desired properties may be used including, but not limited to, ethyl acetate, tetrahydrofuran, acetonitrile, or methyl tert-butyl ether.

The DNAZ HBr may be separated from the ABDNAZ by an aqueous extraction. The ABDNAZ may then be crystallized directly from the solvent by adding the nonsolvent and removing the solvent. As used herein, the term "nonsolvent" means and includes an organic solvent in which the ABDNAZ is substantially insoluble. The nonsolvent and the solvent may be substantially miscible with one another. While embodiments herein describe the nonsolvent as ethanol, other organic solvents having the desired properties may be used, such as methanol, isopropanol, or an alkane, such as heptane. Coproducts or byproducts produced by the reaction may be more soluble than the ABDNAZ in the nonsolvent. As such, residual coproducts and other impurities are removed with subsequent washes of nonsolvent. Recovery of the ABDNAZ in this manner may reduce the number of recrystallization and washing acts utilized in the overall method of synthesizing and isolating ABDNAZ.

In the oxidative nitration reaction, HMNAZ may be used as a starting material to produce DNAZ. HMNAZ is commercially available from Parish Chemical Company (Vineyard, Utah). The HMNAZ may initially be reacted with sodium hydroxide in water. The ratio of sodium hydroxide to HMNAZ used in the oxidative nitration reaction may be at least 1:1. However, to ensure dissolution of the HMNAZ, an excess of sodium hydroxide may be used relative to the HMNAZ. By way of non-limiting example, up to approximately 3.5 mole equivalents of sodium hydroxide may be used per one mole equivalent of HMNAZ. The HMNAZ, sodium hydroxide, and water may form an aqueous nitronate solution. The aqueous nitronate solution may be dilute to minimize and control exotherms that occur during the oxidative nitration reaction. Excess sodium hydroxide may also be present to ensure complete formation of the nitronate salt and to maintain basic conditions during the oxidative nitration reaction. The sodium hydroxide may be added to the water with stirring, producing a sodium hydroxide solution. For all stirring acts described herein, the reagents may be stirred using overhead stirrers or magnetic stir bars, depending on the volume of reagents being added. The stirring rate may be sufficient to dissolve or suspend the reagents in the medium to which they are added. Since the addition of sodium hydroxide to water is exothermic, the sodium hydroxide solution may be cooled to approximately 25° C. before additional acts are conducted. Within four hours of producing the sodium hydroxide solution, the HMNAZ may be added to the sodium hydroxide solution, which is maintained at a temperature of between approximately 20° C. and approximately 27° C. during the addition. The HMNAZ may be stirred with the sodium hydroxide solution for from approximately one hour to approximately two hours, forming the nitronate solution. The nitronate solution may be prepared and stored for up to approximately two hours or longer before adding additional reagents used in the oxidative nitration reaction. At least one hour after the addition of the HMNAZ, the nitronate solution may be cooled to less than or equal to approximately 10° C.

An aqueous solution of sodium nitrite and potassium ferricyanide may be prepared by dissolving the sodium nitrite and potassium ferricyanide in water. The sodium nitrite/potassium ferricyanide solution may be stirred for up to approximately three hours. Excess water may be utilized to produce a dilute solution so that exotherms that subsequently occur during the oxidative nitration reaction may be easily controlled using an ice bath. The potassium ferricyanide may be utilized in the oxidative nitration reaction at a catalytic concentration, such as from approximately 5 mole % to approximately 15 mole % with respect to HMNAZ. The sodium nitrite may be used at from approximately 1 mole equivalent to approximately 4 mole equivalents per mole equivalent of HMNAZ to ensure complete conversion of the HMNAZ to DNAZ. The sodium nitrite and potassium ferricyanide are stable in aqueous solution and do not significantly react with each other, so the aqueous solution of sodium nitrite and potassium ferricyanide may be prepared and stored for up to approximately three hours.

The sodium nitrite/potassium ferricyanide solution may be added to the cooled (less than or equal to approximately 10° C.) nitronate solution. Since an increase in temperature (from approximately 0° C. to approximately 15° C.) is expected upon addition, the nitronate solution is cooled so that the resulting maximum exotherm does not exceed approximately 30° C. However, due to the dilute nature of both solutions, the maximum exotherm expected when the two solutions are combined is approximately 20° C., even if the solutions are rapidly combined. After the addition, the combination of the sodium nitrite/potassium ferricyanide solution and the nitronate solution may be cooled to less than or equal to approximately 15° C., such as from approximately 10° C. to approximately 15° C. Sodium persulfate may then be added. The sodium persulfate may be used at from approximately 1 mole equivalent to approximately 2 mole equivalents per mole equivalent of HMNAZ. The addition of the sodium persulfate may be completed within approximately thirty minutes after combining the sodium nitrite/potassium ferricyanide solution with the nitronate solution to ensure minimal decomposition of the nitronate. After the addition of the sodium persulfate, the temperature of the reaction mixture may be maintained at less than or equal to approximately 15° C. to prevent the resulting exotherm from increasing the temperature of the reaction mixture above approximately 30° C. The temperature of the reaction mixture may initially drop approximately 5° C. before the exotherm of between approximately 5° C. and approximately 20° C. occurs. The temperature of the reaction mixture may be maintained using a cold bath. The cold bath may be removed once the temperature of the reaction mixture stops increasing. After removing the cold bath, the oxidative nitration reaction may proceed with stirring for at least approximately one hour. If the surrounding environment in which the oxidative nitration reaction is conducted is subject to temperature fluctuations, the temperature of the surrounding environment may be monitored to ensure that the temperature of the oxidative nitration reaction does not increase to a temperature of greater than approximately 30° C.

The oxidative nitration reaction produces DNAZ and water-soluble byproducts. The DNAZ may be extracted from the biphasic oxidative nitration reaction solution using multiple washes of a solvent. The volume of solvent used may be sufficient to effectively extract the DNAZ. The solvent may be an organic solvent in which DNAZ is substantially soluble but in which the byproducts of the oxidative nitration reaction are substantially insoluble. For simplicity and convenience, the solvent used to extract the DNAZ from the oxidative nitration reaction solution may be the same solvent in which the DNAZ, bromoacetyl bromide, and boron trifluoride etherate are reacted. The aqueous phases from the extraction, which include the byproducts of the oxidative nitration reaction, may be discarded, while the organic (solvent) phases are collected and combined. The aqueous phases from the extraction may include sodium hydroxide, potassium ferricyanide, sodium nitrite, or sodium sulfate dissolved in the water. The organic phase includes the DNAZ and may be dried with a drying agent, such as anhydrous sodium sulfate or anhydrous magnesium sulfate. The organic phase is referred to herein as the DNAZ/solvent solution. To ensure that the DNAZ/solvent solution is dry (i.e., substantially free of water), a sufficient amount of the drying agent may be added to the DNAZ/solvent solution until solid drying agent is free flowing in solution. The drying agent may be removed from the DNAZ/solvent solution by vacuum filtration. By way of non-limiting example, when dichloromethane is used as the solvent, DNAZ/dichloromethane solutions have been determined to include 0.142% water prior to drying with the drying agent, compared to 0.091% water after drying. The oxidative nitration reaction may produce the DNAZ at a yield of from approximately 80% to approximately 100% (based on HMNAZ). The purity of the DNAZ, as determined by high performance liquid chromatography (HPLC), is greater than approximately 97%.

If the DNAZ is to be stored before subsequent acts are conducted, at least a portion of the solvent may be removed, such as by evaporation under reduced pressure, fanning a concentrated DNAZ/solvent solution. If substantially all of the solvent is removed, the resulting DNAZ may be in a liquid state at ambient conditions. As described herein, acts that involve evaporation under reduced pressure may be conducted at vacuum levels and for an amount of time sufficient that the respective solution or suspension is not exposed to a temperature of greater than or equal to approximately 30° C. for greater than or equal to approximately ten hours. The concentrated DNAZ/solvent solution or DNAZ may be stored at a temperature ranging from approximately 0° C. to approximately 30° C. for up to approximately ninety-six hours or greater. Since decomposition of the DNAZ is known to occur at a temperature greater than approximately 75° C., the DNAZ/solvent solution may be maintained at a temperature below approximately 30° C. to ensure little or no decomposition.

If the DNAZ has been stored neat, an additional volume of solvent may be added to the DNAZ. Before converting the DNAZ to ABDNAZ, the DNAZ/solvent solution may be purged with an anhydrous inert gas, such as nitrogen, to minimize the presence of water. Water may be present as moisture in air from the relative humidity of the surrounding environment. Water, if present, may affect the activity of the boron trifluoride etherate or may react with bromoacetyl bromide, which is sensitive to hydrolysis reactions. The DNAZ/solvent solution may be reacted with bromoacetyl bromide in the presence of the boron trifluoride etherate, producing the ABDNAZ, as shown in FIG. 2. As the reaction occurs, the majority of ABDNAZ remains in solution in the solvent, while the majority of DNAZ HBr precipitates as a solid. Therefore, the ABDNAZ reaction mixture is heterogeneous. The boron trifluoride etherate and bromoacetyl bromide may be added to the DNAZ/solvent solution within a time period of approximately fifteen minutes. Two molar equivalents of the DNAZ may be reacted with 1.5 molar equivalents of bromoacetyl bromide in the solvent. In contrast, in the Bednarski process, a stoichiometric amount of bromoacetyl bromide (one-half molar equivalent) was used per molar equivalent of DNAZ. A catalytic amount of the boron trifluoride etherate may be used in the method of the present invention, such as from approximately 5 mole % to approximately 15 mole % with respect to DNAZ. While embodiments herein describe adding the boron trifluoride etherate and then the bromoacetyl bromide, the reagents may be added in any order. Since the addition of boron trifluoride etherate and bromoacetyl bromide is not significantly exothermic, and because this reaction is heated to reflux, the rate of addition of these reagents does not substantially affect the yield or purity of the ABDNAZ obtained. The ABDNAZ reaction mixture may be heated to a mild reflux and stirred for from approximately four hours to approximately seven hours until the majority of the DNAZ has been converted to ABDNAZ, at which point the heat is removed. In contrast, in the Bednarski process, the reflux was conducted for two hours. In an embodiment of the invention, the temperature to which the ABDNAZ reaction mixture is heated is below the boiling point of the solvent. By way of non-limiting example, if dichloromethane is used as the solvent, the ABDNAZ reaction mixture may be heated to less than approximately 40° C. during the course of the reaction. The ABDNAZ reaction mixture may also include DNAZ HBr, which, in dry solid form, is sensitive to impact, friction, and other external stimuli. One stoichiometric equivalent of DNAZ HBr is generated per mole-equivalent of ABDNAZ. The DNAZ HBr may be a white/yellow solid. The ABDNAZ reaction mixture may also include HBr and up to approximately 20% of unreacted DNAZ, which is removed as explained below.

After completion of the reaction, an additional volume of the solvent and water may be added to the ABDNAZ reaction mixture and stirred for from approximately one hour to approximately twenty-four hours. The volume of solvent and water added may be sufficient to dissolve the DNAZ HBr in the water and any precipitated ABDNAZ in the solvent. Since DNAZ HBr is water soluble, the DNAZ HBr may partition into the aqueous phase while the ABDNAZ remains in the organic (solvent) phase. The organic and aqueous phases may then be separated, such as by conventional liquid-liquid separation techniques, and the aqueous phase discarded. The organic phase including the ABDNAZ is referred to herein as an ABDNAZ/solvent solution. Since the DNAZ HBr remains in aqueous solution during the separation, the DNAZ HBr may be easily disposed of. By eliminating handling of the DNAZ HBr in solid form, ABDNAZ may be synthesized and isolated by a non-energetic process. As a consequence, manufacturers of ABDNAZ do not need to be certified or qualified to handle explosive compounds. In addition, conventional equipment and facilities may be used to produce the ABDNAZ, which reduces the cost and complexity of its synthesis and isolation. In contrast, in the Bednarski process, solid DNAZ HBr is removed by filtration.

The ABDNAZ/solvent solution may be washed with multiple portions of water to remove any trace amounts of the DNAZ HBr. During the water washes, additional solvent may be added to the ABDNAZ/solvent solution to prevent the ABDNAZ from crystallizing. The volume of water or solvent added may be sufficient to remove or extract the desired compounds. The purity of the ABDNAZ/solvent solution may be monitored by proton nuclear magnetic resonance ($^1$H NMR) to verify that substantially all of the DNAZ HBr has been removed. If DNAZ HBr remains in the ABDNAZ/solvent solution, additional water washes may be conducted until the ABDNAZ/solvent solution is determined to be substantially free of DNAZ HBr. The volume of water used may be sufficient to extract the desired compounds. By way of non-limiting example, the ABDNAZ/solvent solution may include less than approximately 0.4% DNAZ HBr after washing with the water. The ABDNAZ/solvent solution may be dried with a drying agent, such as with sodium sulfate, until the solid is free flowing in solution. The drying agent may be removed by vacuum filtration. The ABDNAZ/solvent solution may be concentrated, such as by evaporation under reduced pressure, to remove approximately half of the volume of the ABDNAZ/solvent solution.

To crystallize the ABDNAZ, a sufficient volume of the nonsolvent may be added to the ABDNAZ/solvent solution, forming an ABDNAZ/solvent/nonsolvent mixture. Addition of the nonsolvent to the ABDNAZ/solvent solution enables the ABDNAZ to be crystallized at a high purity in the nonsolvent. Any coproducts or byproducts remaining in the ABDNAZ/solvent/nonsolvent mixture may be soluble in the nonsolvent. The coproducts include, but are not limited to, DNAZ HBr, while the byproducts include, but are not limited to, DNAZ, bromoacetic acid, and sodium sulfate. The nonsolvent may be an organic solvent in which ABDNAZ is substantially insoluble and having a boiling point sufficiently higher than that of the solvent such that removal of the solvent is readily achieved. The ABDNAZ may also be substantially unreactive with the nonsolvent at the temperature used to crystallize the ABDNAZ. The nonsolvent may be a relatively non-toxic organic material since the ABDNAZ will be administered to humans or other mammals.

The addition of the nonsolvent to the ABDNAZ/solvent solution may alter the solubility of the ABDNAZ. Specifically, the solubility of the ABDNAZ may be reduced when the nonsolvent is added to the ABDNAZ/solvent solution. The solubility of the ABDNAZ in the ABDNAZ/solvent/nonsolvent mixture may be further altered by removing the solvent, such as by evaporating the solvent under reduced pressure (i.e., using a rotary evaporator). The rate at which the solvent is removed may affect the crystallization of the ABDNAZ. If the solvent is removed quickly, the ABDNAZ may form as an amorphous solid material having impurities trapped therein. In contrast, if the solvent is removed slowly, the ABDNAZ may crystallize in a more pure form. As the solvent is removed, the volume of the ABDNAZ/solvent/nonsolvent mixture decreases, enabling the ABDNAZ to precipitate and form an ABDNAZ/nonsolvent suspension. The removal of the solvent may be stopped when the volume of liquid remaining in the ABDNAZ/nonsolvent suspension is just sufficient to cover the surface of the ABDNAZ during rotation of the rotary evaporator. The ABDNAZ/nonsolvent suspension may be cooled to approximately 0° C. for approximately thirty minutes and the crystals of ABDNAZ recovered, such as by vacuum filtration. The ABDNAZ may be obtained as clear, colorless or white crystals. The ABDNAZ may be rinsed with additional volumes of chilled nonsolvent to ensure that substantially all impurities are removed from the ABDNAZ. The nonsolvent filtrate may then be discarded. The ABDNAZ may be stored under vacuum, and or air may be pulled through the ABDNAZ on a filter for from approximately one hour to approximately sixteen hours to ensure that substantially no residual solvent, nonsolvent, or water remains. In contrast, in the Bednarski process, crude ABDNAZ is isolated by the evaporation of dichloromethane; the crude ABDNAZ is then washed with a biphasic diethyl ether rinse, providing ABDNAZ of approximately 98% purity.

The ABDNAZ synthesized and isolated by the method of the present invention may have a purity of greater than approximately 99.5% (as determined by HPLC). In contrast, the ABDNAZ synthesized and isolated by the Bednarski process is approximately 98% pure, with the remaining 2% including bromoacetic acid, unreacted DNAZ, and DNAZ HBr. The ABDNAZ produced by the method of the present invention is also whiter in color compared to the yellowish color of the ABDNAZ produced by the Bednarski process. The yield of the ABDNAZ produced by the method of the present invention may be from approximately 80% to approximately 100% based on DNAZ (assuming 100% yield of DNAZ from HMNAZ).

In one embodiment of the present invention, dichloromethane is used as the solvent and ethanol is used as the nonsolvent. Without being bound to a particular theory, it is believed that using dichloromethane and ethanol provides effective isolation of the ABDNAZ because the difference in their boiling points enables the dichloromethane to be removed by evaporation at low temperature while the ethanol remains for crystallizing the ABDNAZ. In addition, the temperature during the crystallization is sufficiently low that substantially no reaction occurs between the ABDNAZ and ethanol. The use of ethanol to successfully crystallize the ABDNAZ in the method of the present invention was unexpected because previous attempts to recrystallize ABDNAZ using ethanol at elevated temperatures (refluxing ethanol) resulted in the formation of two new impurities. However, the temperature during the crystallization of the method of the present invention is sufficiently high to remove the dichloromethane. Even with the potential reactivity between the ABDNAZ and ethanol, ethanol was found to be a good nonsolvent for recrystallization because the ABDNAZ was produced at a high yield and purity. Furthermore, ethanol is substantially less toxic to humans and animals relative to dichloromethane.

The ability of the aqueous extraction to effectively remove DNAZ HBr from the ABDNAZ reaction mixture was unexpected because DNAZ HBr was expected to have limited solubility in water. However, in qualitative experiments, the DNAZ HBr was determined to be significantly more soluble in water than the ABDNAZ. ABDNAZ has a solubility in water of from approximately 0.3 mg/ml to approximately 1.3 mg/ml, and a solubility of approximately 30 mg/ml in dichloromethane. The appreciable solubility of DNAZ HBr in water was surprising since a significant portion of DNAZ HBr includes non-polar, carbon and hydrogen moieties, which, conventionally, are not soluble in water. Based on the structural similarity between DNAZ HBr and ABDNAZ (see FIG. 2), DNAZ HBr and ABDNAZ were expected to have comparable solubilities in the solvent and water. Although it is a salt, a greater percentage of the molecular weight of DNAZ HBr is attributable to carbon and hydrogen atoms than ABDNAZ, suggesting the two compounds would have similar solubilities in water. Furthermore, DNAZ HBr was not expected to be sufficiently soluble in water to enable aqueous extraction.

Therefore, the significantly different solubilities of ABDNAZ and DNAZ HBr in the solvent versus the water were not expected.

The aqueous extraction also, unexpectedly, improved the yield and purity of the ABDNAZ produced compared to the yield and purity of the ABDNAZ produced by the Bednarski process. Without being bound by any particular theory, it is believed that the aqueous extraction conducted on the ABDNAZ reaction mixture forces the ABDNAZ and DNAZ HBr to dissolve separately in the organic phase (solvent) and the aqueous phase (water), respectively. Since ABDNAZ is significantly more soluble in the solvent than in water, ABDNAZ remains in the organic phase. Conversely, since DNAZ HBr is significantly more soluble in water than in the solvent, the DNAZ HBr partitions into the aqueous phase. Since the solubilities of the ABDNAZ and DNAZ HBr in solvent and in water are sufficiently different, a minimal amount of ABDNAZ may become trapped in the aqueous phase and a minimal amount of DNAZ HBr may become dissolved in the solvent. Thus, the ABDNAZ ultimately recovered from the ABDNAZ/solvent solution may be relatively pure and may be isolated at a relatively high yield.

In addition, using an aqueous extraction to effectively separate the ABDNAZ and DNAZ HBr was unexpected because ABDNAZ is slightly reactive toward water. It was expected that exposing the ABDNAZ to water would produce undesirable hydrolysis byproducts. However, the water was observed to dissolve the DNAZ HBr without substantially reacting with the ABDNAZ under these conditions.

Figure 3:
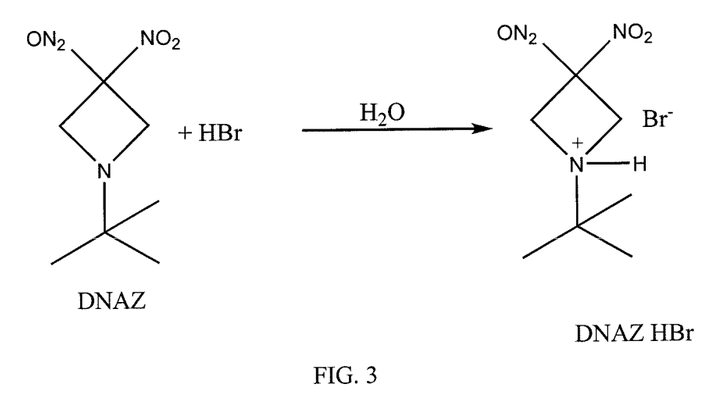
FIG. 3 illustrates the reaction of DNAZ with aqueous hydrogen bromide (HBr) to produce the HBr salt of DNAZ (DNAZ HBr).

An additional advantage to using the aqueous extraction and aqueous washes to separate the ABDNAZ and the DNAZ HBr is the potential to remove unreacted DNAZ from the ABDNAZ reaction mixture. The unreacted DNAZ may be present in the ABDNAZ reaction mixture at up to approximately 20%. The unreacted DNAZ may react with aqueous HBr to form additional DNAZ HBr, as shown in FIG. 3. The HBr may be present in the ABDNAZ reaction mixture as a byproduct of the conversion of DNAZ to ABDNAZ. Alternatively, the aqueous HBr that reacts with the DNAZ may be provided as a solution of HBr in water. The aqueous HBr solution may include from approximately 1% HBr to approximately 48% HBr. By way of non-limiting example, one of the water washes conducted on the ABDNAZ reaction mixture or on the ABDNAZ/solvent solution may be replaced with a wash including the aqueous HBr solution. Since the additional DNAZ HBr produced is water soluble, the DNAZ HBr may be easily removed from the ABDNAZ reaction mixture or the ABDNAZ/solvent solution by subsequent aqueous extractions or aqueous washes. Removing the unreacted DNAZ at an early stage in the synthesis and isolation of ABDNAZ, as in the method of the present invention, enables the ABDNAZ to be produced at a higher purity and yield compared to the Bednarski process. In the Bednarski process, the unreacted DNAZ remains in the dichloromethane and gets trapped in the ABDNAZ as the solvent is removed under vacuum. The DNAZ is then only partially removed by diphasic ether washes. Ultimately, the total number of crystallization and wash acts utilized to synthesize and isolate the ABDNAZ from HMNAZ by the method of the present invention may be reduced compared to those of the Bednarski process.

A therapeutically effective amount of the ABDNAZ produced by the method of the present invention may be formulated into a pharmaceutical composition, as described in Bednarski. The pharmaceutical composition may include a pharmaceutically acceptable vehicle, the ABDNAZ, and optionally, at least one of a wetting or emulsifying agent, a pH buffering agent, an auxiliary agent, a stabilizing agent, a suspending agent, a dispersing agent, a solubilizing agent, a thickening agent, a lubricating agent, a coloring agent, a sweetening agent, a flavoring agent, or a preserving agent. The pharmaceutical composition may include a pharmaceutically active agent or therapeutic agent in addition to the ABDNAZ. The pharmaceutical composition may be administered to a patient, such as a human or other mammal, for the treatment or prevention of a disease or disorder characterized by abnormal cell proliferation, as described in Bednarski.

The following examples serve to explain embodiments of the present invention in more detail. These examples are not to be construed as being exhaustive, exclusive, or otherwise limiting as to the scope of this invention.

EXAMPLES

Solvents and reagents used in the synthesis and isolation of ABDNAZ were purchased from commercial sources, such as from Sigma-Aldrich Co. (St Louis, Mo.) or Parish Chemical Company (Vineyard, Utah). The sodium hydroxide, potassium ferricyanide, sodium nitrite, sodium persulfate, dichloromethane, sodium sulfate, and ethanol were of reagent grade. Boron trifluoride etherate was of redistilled grade. Bromoacetyl bromide was 98+% purity. Distilled water was used in the synthesis and isolation of ABDNAZ. The HMNAZ was greater than or equal to 98% purity.

The ABDNAZ was manufactured according to Good Laboratory Practices (GLP). Dedicated glassware and processing aids were used in the synthesis and isolation of ABDNAZ. All equipment used was cleaned by rinsing with at least one of distilled water and an organic solvent.

Except where otherwise indicated, the synthesis and isolation of ABDNAZ was conducted with minimal down time between successive reactions or acts. As used herein, the term "ambient" refers to atmospheric pressure and a temperature ranging from approximately 20° C. to approximately 30° C. To prevent decomposition during the synthesis and isolation of ABDNAZ, the respective solution or suspension is not exposed to a temperature of greater than 30° C. for greater than approximately ten hours.

The properties shown in Table 1 were measured or determined by conventional techniques, which are not described in detail herein. The purity of ABDNAZ was measured by infrared (IR) spectroscopy, HPLC, or NMR spectroscopy. Thermal stability was measured by differential scanning calorimetry (DSC) using a temperature ramp rate of 20° C./minute. The thermal stability is reported as the temperature of the onset of melting and the temperature of the onset of decomposition. The melting point is reported as the temperature of the onset of melting. The elemental analysis was measured by conventional techniques.

Example 1

Synthesis of DNAZ from HMNAZ

An Erlenmeyer flask equipped with a magnetic stir bar was charged with water (400 mL), potassium ferricyanide (17.2 g, 52 mmol), and sodium nitrite (143.2 g, 2075 mmol). The solution (referred to herein as "Solution A") was stirred until all solids dissolved (approximately fifteen minutes).

A round-bottom flask equipped with a magnetic stir bar and a thermocouple was charged with distilled water (1470 mL) and, while stirring, sodium hydroxide (71.2 g, 1780 mmol). Using a cold bath, the aqueous sodium hydroxide solution was returned to ambient temperature (20° C. to 30° C.) and HMNAZ (97.6 g, 519 mmol) was added. The nitronate solution was stirred at ambient conditions for from approximately one hour to approximately two hours, during which time nearly all solids dissolved. This solution is referred to herein as "Solution B". Solution B was chilled to 10° C. and then Solution A was added. With the temperature at between approximately 10° C. and approximately 15° C., sodium persulfate (173.2 g, 727 mmol) was introduced to the round-bottom flask over a period of from approximately one minute to approximately two minutes. After the exotherm began to subside, the cold bath was removed and the reaction mixture was stirred at ambient conditions for approximately sixteen hours. The resulting orange/brown liquid was added to a separatory funnel and extracted with dichloromethane (3×450 mL). The combined organic extracts were dried with sodium sulfate (approximately 100 g), added to a round-bottom flask, and concentrated to approximately 450 mL using a rotary evaporator.

Example 2

Synthesis of ABDNAZ from DNAZ

A three-neck round-bottom flask (3 L) equipped with a magnetic stir bar and a water jacketed reflux condenser was charged with the dichloromethane solution of DNAZ (produced as described in Example 1). A nitrogen gas purge of the apparatus was initiated and, after ten minutes, boron trifluoride diethyletherate (6.37 mL, 52 mmol) was added, followed by bromoacetyl bromide (33.77 mL, 388 mmol). The flask was sealed, except for a small vent at the top of the condenser, and the solution was heated to a mild reflux. After six hours (±0.5 hour), heating was stopped and dichloromethane (1000 mL) and distilled water (800 mL) were added, in that order, to the heterogeneous mixture. The two-phase system was stirred vigorously for sixteen hours, until all solids (DNAZ HBr) were dissolved. The two-phase system was then transferred to a separatory funnel. The aqueous phase was removed and the organic phase was washed with additional distilled water (4×500 mL). The organic phase was dried with sodium sulfate (100 g-150 g) and then transferred to a single-neck, round-bottom flask. The solution was concentrated on a rotary evaporator to approximately half of its initial volume and then ethanol (250 mL) was added. The remaining dichloromethane was removed by a rotary evaporator, causing precipitation of clear, colorless crystals. The flask was chilled in an ice bath for thirty minutes. The precipitate was isolated by vacuum filtration, rinsed with additional cold ethanol (5×150 mL), and dried to afford pure ABDNAZ (56.04 g, 81% yield): $^1$H NMR ($d_6$-acetone) δ 4.02 (s, 2H, —CH$_2$Br), 4.96 (br s, 2H, ring —CH$_2$), 5.36 (br s, 2H, ring —CH$_2$); $^{13}$C NMR ($d_6$-acetone) δ 25.58, 58.58, 60.53, 107.69, 167.48.

Example 3

Table 1 lists properties of two samples of ABDNAZ prepared by the method of the present invention and ABDNAZ prepared by the Bednarski process.

TABLE 1

Comparison of ABDNAZ prepared by the method of the present invention and the Bednarski process.

| Property | Inventive Method Sample 1 | Inventive Method Sample 2 | Bednarski Process |
|---|---|---|---|
| Identification (IR) | Positive match | Positive match | Positive match |
| Identification | Positive match | Positive match | Positive match |
| (HPLC) | | | |
| Assay | 100.7% | 100.1% | 98.7% |
| Impurities | | | |
| NaBr | 0.015% | 0.014% | 0.41% |
| Bromoacetic acid | ND | ND | 0.48% |
| DNAZ | ND | ND | 0.48% |
| Total unspecified impurities | 0.033% | 0.031% | 0.31% |
| Total impurities | 0.048% | 0.045% | 1.68% |
| Moisture | 0.038% | 0.009% | 0.05% |
| Residual solvents | | | |
| Dichloromethane | 0.172% | 0.139% | <0.5% (Pass) |
| Ethanol | 0.015% | 0.006% | <0.5% (Pass) |
| Residual on ignition | 0.09% | 0.05% | 0.05% |

ND = not detectable

As shown in Table 1, the ABDNAZ produced by the method of the present invention had fewer impurities (higher purity) compared to the ABDNAZ prepared by the Bednarski process. While even small improvements in purity may oftentimes be difficult to achieve, these improvements may be especially important when a chemical compound is to be used in a pharmaceutical composition. The method of the present invention also reduces the number of processing acts utilized to obtain pure ABDNAZ and also eliminates hazards associated with handling the dry solid explosive DNAZ HBr.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention encompasses all modifications, equivalents, and alternatives falling within the scope of the invention as defined by the following appended claims and their legal equivalents.

What is claimed is:

1. A method of producing N-(bromoacetyl)-3,3-dinitroazetidine (ABDNAZ), comprising:
   reacting 1-tert-butyl-3,3-dinitroazetidine (DNAZ) with bromoacetyl bromide and boron trifluoride etherate to produce a reaction mixture comprising ABDNAZ and a salt of DNAZ;
   adding water and a solvent to the reaction mixture to form an organic phase comprising the ABDNAZ and an aqueous phase comprising the salt of DNAZ;
   separating the organic phase and the aqueous phase to produce an ABDNAZ/solvent solution comprising the ABDNAZ and the aqueous phase comprising the salt of DNAZ;
   adding a nonsolvent to the ABDNAZ/solvent solution to produce an ABDNAZ/solvent/nonsolvent mixture, the nonsolvent comprising an organic solvent; and
   recovering the ABDNAZ.

2. The method of claim 1, wherein reacting DNAZ with bromoacetyl bromide and boron trifluoride etherate to produce a reaction mixture comprising ABDNAZ and a salt of DNAZ comprises reacting the DNAZ, bromoacetyl bromide, and boron trifluoride etherate at reflux and for a time period of from approximately four hours to approximately seven hours.

3. The method of claim 1, wherein reacting DNAZ with bromoacetyl bromide and boron trifluoride etherate to produce a reaction mixture comprising ABDNAZ and a salt of DNAZ comprises reacting DNAZ with bromoacetyl bromide and boron trifluoride etherate in a solvent.

4. The method of claim 3, wherein reacting DNAZ with bromoacetyl bromide and boron trifluoride etherate in a solvent comprises reacting DNAZ with bromoacetyl bromide and boron trifluoride etherate in dichloromethane.

5. The method of claim 3, wherein reacting DNAZ with bromoacetyl bromide and boron trifluoride etherate in a solvent comprises reacting two molar equivalents of DNAZ with 1.5 molar equivalents of bromoacetyl bromide in dichloromethane.

6. The method of claim 1, wherein adding water and a solvent to the reaction mixture to form an organic phase and an aqueous phase comprises adding dichloromethane and water to the reaction mixture to form the organic phase comprising the ABDNAZ and the aqueous phase comprising the salt of DNAZ.

7. The method of claim 1, further comprising washing the ABDNAZ/solvent solution with water before adding the nonsolvent.

8. The method of claim 7, further comprising adding a drying agent to the ABDNAZ/solvent solution to remove water and recovering the drying agent.

9. The method of claim 8, further comprising removing at least a portion of the solvent from the ABDNAZ/solvent solution.

10. The method of claim 1, wherein adding a nonsolvent to the ABDNAZ/solvent solution comprises adding ethanol to the ABDNAZ/solvent solution.

11. The method of claim 1, wherein recovering the ABDNAZ comprises removing the solvent from the ABDNAZ/solvent/nonsolvent mixture to form an ABDNAZ/nonsolvent suspension.

12. The method of claim 11, further comprising removing the nonsolvent from the ABDNAZ/nonsolvent suspension to produce crystals of the ABDNAZ.

13. A method of producing N-(bromoacetyl)-3,3-dinitroazetidine (ABDNAZ), comprising:
reacting 1-tert-butyl-3,3-dinitroazetidine (DNAZ) with bromoacetyl bromide and boron trifluoride etherate in dichloromethane to produce a reaction mixture comprising ABDNAZ and a hydrogen bromide salt of DNAZ;
adding water and an additional volume of dichloromethane to the reaction mixture to form an organic phase comprising the dichloromethane and the ABDNAZ and an aqueous phase comprising the water and the hydrogen bromide salt of DNAZ;
separating the organic phase from the aqueous phase;
adding ethanol to the organic phase comprising the dichloromethane and the ABDNAZ;
evaporating the dichloromethane under reduced pressure to form an ABDNAZ/ethanol suspension; and
filtering the ethanol from the ABDNAZ/ethanol suspension.

14. The method of claim 13, wherein filtering the ethanol from the ABDNAZ/ethanol suspension comprises producing ABDNAZ at a yield of from approximately 80% to approximately 100% based on an assumed 100% yield of DNAZ from 1-tert-butyl-3-hydroxymethy-3-nitroazetidine (HMNAZ).

15. The method of claim 13, wherein filtering the ethanol from the ABDNAZ/ethanol suspension comprises producing ABDNAZ having a purity of greater than approximately 99.5%.

16. The method of claim 15, wherein producing ABDNAZ having a purity of greater than approximately 99.5% comprises producing ABDNAZ substantially free of a salt of 1-tert-butyl-3,3-dinitroazetidine.

17. The method of claim 15, wherein producing ABDNAZ having a purity of greater than approximately 99.5% comprises producing ABDNAZ comprising less than approximately 0.4% 1-tert-butyl-3,3-dinitroazetidine.

* * * * *

UNITED STATES PATENT AND TRADEMARK OFFICE
CERTIFICATE OF CORRECTION

PATENT NO.         : 8,471,041 B2
APPLICATION NO.    : 12/702782
DATED              : June 25, 2013
INVENTOR(S)        : Nicholas A. Straessler et al.

It is certified that error appears in the above-identified patent and that said Letters Patent is hereby corrected as shown below:

On the title page:
In ITEM (56) References Cited:
    U.S. PATENT DOCUMENTS
    Page 1, $1^{st}$ column, $7^{th}$ entry, line 47,    change "Biesalki" to --Biesalski--

In ITEM (56) References Cited:
    OTHER PUBLICATIONS
    Page 3, $1^{st}$ column,
    line 50,    change "Materiel" to --Material--

In the claims:
CLAIM 14, COLUMN 14, LINE 24,    change "hydroxymethy" to --hydroxymethyl--

Signed and Sealed this
Thirtieth Day of September, 2014

Michelle K. Lee
*Deputy Director of the United States Patent and Trademark Office*